United States Patent [19]

Mazurek

[11] Patent Number: 4,925,996
[45] Date of Patent: May 15, 1990

[54] TWO STAGE PROCESS FOR CATALYTIC CONVERSION OF OLEFINS TO HIGHER HYDROCARBONS

[75] Inventor: Harry Mazurek, Bala Cynwyd, Pa.

[73] Assignee: Atlantic Richfield Company, Los Angeles, Calif.

[21] Appl. No.: 817,853

[22] PCT Filed: Apr. 26, 1985

[86] PCT No.: PCT/US85/00770

§ 371 Date: Dec. 16, 1985

§ 102(e) Date: Dec. 16, 1985

[87] PCT Pub. No.: WO85/05102

PCT Pub. Date: Nov. 21, 1985

[51] Int. Cl.$^5$ .............................................. C07C 2/12
[52] U.S. Cl. ..................... 585/312; 585/313; 585/322; 585/329; 585/415; 585/422; 585/424; 585/533
[58] Field of Search ............. 585/312, 313, 322, 329, 585/415, 412, 422, 424, 533, 526, 530, 525

[56] References Cited

U.S. PATENT DOCUMENTS

| | | | |
|---|---|---|---|
| 3,960,978 | 6/1976 | Givens et al. | 585/533 |
| 4,451,685 | 5/1984 | Nevitt et al. | 585/415 |
| 4,490,568 | 12/1984 | Garka et al. | 585/415 |
| 4,499,315 | 2/1985 | Garka et al. | 585/322 |
| 4,499,316 | 2/1985 | Garka et al. | 585/322 |
| 4,499,325 | 2/1985 | Klotz et al. | 585/322 |

FOREIGN PATENT DOCUMENTS 2140027  11/1984  United Kingdom ............. 585/415

*Primary Examiner*—Asok Pal
*Attorney, Agent, or Firm*—Craig E. Larson

[57] ABSTRACT

A process is disclosed for converting a feedstock containing ethylene to produce heavier hydrocarbons in the gasoline or distillate boiling range including the steps of contacting the olefins feedstock with a first siliceous crystalline molecular sieve at an elevated temperature and relatively low pressure under conditions which maximize the conversion of ethylene to $C_3$–$C_4$ olefins and $C_5+$ hydrocarbons, separating $C_3$–$C_4$ olefins from the $C_5+$ hydrocarbons, and contacting the separated $C_3$–$C_4$ olefins with a second siliceous crystalline molecular sieve at moderate temperatures under conditions favorable for conversion of the $C_3$–$C_4$ olefins to heavier hydrocarbons in the gasoline or distillate boiling range.

12 Claims, 2 Drawing Sheets

TWO STAGE PROCESS FOR CATALYTIC CONVERSION OF OLEFINS TO HIGHER HYDROCARBONS

TECHNICAL FIELD

This invention relates to a method of catalytically converting olefins into higher hydrocarbons. This invention more particularly relates to a method for converting feedstocks containing ethylene and $C_3+$ olefins to higher hydrocarbons by contact with siliceous crystalline molecular sieves.

BACKGROUND ART

Conversion of various hydrocarbon fractions with acidic catalysts generally and more particularly with siliceous crystalline molecular sieves is well known in the art. The conversions for which such catalysts have been used include cracking, isomerization, hydrocracking, etc. Molecular sieves have also been used for the conversion of hydrocarbon feeds consisting essentially of $C_2$–$C_5$ olefins, mixtures thereof, and mixtures thereof with paraffins to higher molecular weight products.

U.S. Pat. No. 3,325,465 teaches a process for polymerizing olefinic hydrocarbons over zeolites, the initially present cations of which have been partially exchanged with cations selected from the group consisting Co, Ni and rare earth cations. Ethylene polymerization at atmospheric pressure is described in Examples 3–8 of the patent. At column 6, lines 41–47, the patent teaches that use of atmospheric pressure is preferred, although pressures up to 1000 atmospheres may be used. Higher pressures are said to increase throughput but increase the risk of catalyst deactivation. Operating temperatures of 25° to 400° C. and space velocities of 50 to 1000 hr.$^{-1}$ VHSV (volume hourly space velocity), preferably less than 300 hr.$^{-1}$ VHSV, are taught. Hydrocarbon diluents such as paraffins and/or cycloparaffins may be present in the olefinic feedstock, but the patent does not indicate what effect such presence may have on selection of operating parameters for the process.

U.S. Pat. No. 3,760,024 teaches preparation of aromatic compounds by contacting $C_2$–$C_4$ paraffins and/or olefins with a ZSM-5 type zeolite. Operating temperatures of 100°–700° C., operating pressures of 0–1000 psig (preferably 0–500 psig), and space velocities of 0.5–40 hr.$^{-1}$ WHSV (weight hourly space velocity) are taught. The particular combination of operating parameters employed is selected to produce a significant yield of liquid product from a given feedstock, which product is substantially aromatic in nature.

U.S. Pat. No. 3,827,968 discloses an aromatization process wherein the olefin content of a $C_2$–$C_5$ olefin-containing feed is first oligomerized to produce higher molecular weight olefins over a ZSM-5 type zeolite and then contacting the liquid, higher molecular olefins with a zeolite catalyst in a second stage to produce aromatic liquids. The first step of the '968 process differs from the '024 patent in that less severe operating conditions are used to produce a product having a liquid portion consisting principally of $C_5$–$C_9$ olefins. Attempting direct aromatization of certain feedstocks—especially those containing large amounts of paraffins—was apparently found to cause rapid catalyst aging and/or deactivation. Operating conditions employed in the first step of the '968 patent include temperatures of 290°–450° C., pressures up to 800 psig and 0.5–50 hr.$^{-1}$ WHSV. The first stage oligomerization effluent, in addition to olefinic liquids, contains a gas product consisting of a highly paraffinic $C_4-$ stream. In addition, the second stage of the '968 process produces an effluent which may contain up to 50% $C_4-$ paraffins. The $C_4-$ paraffin streams are, according to the '968 patent, preferably recycled to a pyrolysis unit.

U.S. Pat. No. 3,960,978 discloses the conversion of gaseous $C_2$–$C_5$ olefins, either alone or in admixture with paraffins, to a gasoline fraction having no more than about 20 wt. % aromatics by contacting the olefin feed with a ZSM-5 type zeolite having a controlled acid activity (i.e., alpha value) of about 0.1–120. Other oligomerization conditions include temperatures of 260°–480° C. (preferably 290°–450° C.), WHSV of 0.1–25 hr.$^{-1}$ (preferably 0.5–20), and hydrocarbon partial pressures of 0.5 to 40 atmospheres (preferably 0.5–20 atmospheres). An advantage of the process is said to be improved catalyst stability. Example 1 of the patent shows oligomerization of propylene according to the method of the '978 patent. The gaseous product produced was primarily $C_4$ olefins. The patent suggests recycle of the gaseous $C_4$ olefin byproduct to extinction.

U.S. Pat. No. 3,972,832 discloses conversion of aliphatic compounds over phosphorus-containing zeolites. Example 8 of the patent shows that when ethylene is contacted with the phosphorus-containing zeolite at 500° C. and a WHSV of about 1.5, ethylene is converted into propylene and $C_5$ hydrocarbons as the major products. As compared to a zeolite without phosphorus, the olefin/paraffin ratios of the product obtained over the phosphorus-containing zeolite were much higher and the quantity of aromatics produced much less. Also see U.S. Pat. No. 4,044,065 at column 9, lines 32–48.

U.S. Pat. No. 4,021,502 discloses the conversion of gaseous $C_2$–$C_5$ olefins or mixtures thereof with $C_1$–$C_5$ paraffins to higher molecular weight olefins, over ZSM-4, ZSM-12, ZSM-18, chabazate or zeolite beta. The process is operated under conditions selected to give low yields of aromatics. Temperatures are about 230°–650° C. (preferably 290°–540° C.). WHSV is about 0.2–50 (preferably 1–25). Hydrocarbon partial pressures are about 0.1–50 atmospheres (preferably 0.3–20 atmospheres). An advantage of the process is said to be the stability of the zeolite under the conditions employed.

U.S. Pat. No. 4,070,411 discloses the conversion of lower olefins (e.g., ethylene or propylene) over HZSM-11 catalyst to produce a product having a significant isobutane content. The conversion is effected at temperatures of 300°–500° C. and at space velocities of 0.5–100 WHSV.

U.S. Pat. No. 4,100,218 discloses a process for converting ethane to LPG and gasoline and/or aromatic concentrate by passing olefin effluent from the thermal cracking of ethane over a ZSM-5 type zeolite.

U.S. Pat. No. 4,150,062 discloses the conversion of $C_2$–$C_4$ olefins over ZSM-5 type zeolites in the presence of co-fed water. Temperatures are about 230°–430° C. (preferably 290°–400° C.). Pressures range from atmospheric to 1000 psig preferably from atmospheric to 450 psig). The WHSV is about 0.2–20 hr.$^{-1}$.

U.S. Pat. No. 4,211,640 teaches conversion of olefinic gasoline fractions over ZSM-5 type zeolites to produce gasoline (having enhanced gum stability) and fuel oil.

U.S. Pat. No. 4,227,992 discloses a process for selectively reacting $C_3$ and higher olefins from a mixture of the same with ethylene to produce products comprising fuel oil and gasoline. Operating conditions are selected such that the $C_3$ and higher olefins are substantially converted to products comprising fuel oil and gasoline but such that substantially no ethylene will be converted. Generally, operating pressures are within the range of about 100–1000 psig, temperatures are within the range of about 150°–315° C., and space velocities are within the range of about 0.1–10 WHSV (based on the $C_3$ and higher olefins).

U.S. Pat. No. 4,451,685 teaches conversion of lower olefins to gasoline blending stocks over borosilicate catalysts.

U.S. Pat. No. 4,423,268 teaches oligomerization of normally gaseous olefins over essentially alumina-free molecular sieves (e.g., silicalite).

As noted, conversion of olefins to gasoline and/or distillate products over a ZSM-5 type catalyst is known. See the description of U.S. Pat. Nos. 3,960,978 and 4,021,502, supra. U.S. Pat. No. 4,227,992 discloses operating conditions for selective conversion of $C_3+$ olefins and no more than 20% ethylene conversion. Closely related is U.S. Pat. No. 4,150,062 which discloses a process of converting olefins to gasoline components. In such processes for oligomerizing olefins using acidic crystalline zeolites, it is known that process conditions may be varied to favor the formation of either gasoline or distillate range products. At moderate temperatures (i.e., 190°–315° C.) and relatively high pressures (i.e., 42–70 atmospheres) the conversion conditions favor distillate range product having a normal point of at least 165° C. At moderate temperature and relatively lower pressures (i.e., 7–42 atmospheres), the conversion conditions favor gasoline and distillate range products. See U.S. Pat. No. 4,211,640, supra. The distillate mode conditions do not convert a major fraction of ethylene. At higher temperatures (i.e., 285°–370° C.) and moderate pressures (i.e., 4–30 atmospheres) the conversion conditions favor production of an olefinic gasoline comprising hexane, heptene, octene and other $C_6+$ hydrocarbons in good yield. The gasoline mode conditions convert a major fraction of ethylene.

U.S. Pat. No. 4,433,185 discloses a process for converting an olefinic feedstock containing ethylene and $C_3+$ olefins to produce a heavier hydrocarbon product rich in distillate by contacting the feedstock with an oligomerization catalyst bed at elevated pressure and temperature conditions in an operating mode favorable to the formation of heavy distillate product by selective conversion of $C_3+$ alkenes. The distillate mode effluent stream contains substantially unconverted ethylene which is recovered from the distillate mode effluent stream and further converted to olefinic gasoline in a second oligomerization catalyst bed at reduced moderate pressure and elevated temperature conditions in an operating mode favorable to the formation of $C_6+$ olefinic gasoline. At least a portion of the olefinic gasoline is recycled for conversion with the feedstock in the distillate mode catalyst bed.

U.S. Pat. No. 4,414,423 discloses a process for preparing high boiling hydrocarbons from normally gaseous olefins which comprising contacting a feed comprising normally gaseous olefins with an intermediate pore size siliceous crystalline molecular sieve to produce a first effluent comprising normally liquid olefins and contacting at least a part of the normally liquid olefins contained in the first effluent with a second catalyst comprising an intermediate pore size siliceous molecular sieve under oligomerization conditions to produce a second effluent comprising oligomers of the normally liquid olefins and wherein at least some of said oligomers are liquids under the oligomerization conditions.

One object of the present invention is an improved method for converting ethylene and $C_3+$ olefins to high yields of heavier hydrocarbons. A more particular object is the production of high yields of normally liquid hydrocarbons from such a feedstock, employing a siliceous crystalline molecular sieve catalyst which is relatively stable under the conditions employed. Other objects, aspects and the several advantages of the present invention will be apparent to those skilled in the art upon consideration of the following description of this invention and of the appended claims.

DISCLOSURE OF THE INVENTION

In accordance with the present invention there is provided a process for producing normally liquid hydrocarbons which process comprises: contacting a feedstock containing ethylene and $C_3+$ olefins in a first catalyst reactor zone with a siliceous crystalline molecular sieve at elevated temperature and relatively low ethylene partial pressures under conditions which maximize: (1) ethylene conversion and (2) selectivity to propylene, butylenes, and normally liquid $C_5+$ hydrocarbons; separating the first reactor zone effluent to form at least one normally liquid $C_5+$ hydrocarbon fraction and at least one fraction comprising $C_3$-$C_4$ olefins; and contacting said $C_3$-$C_4$ olefinic fraction in a second reactor zone with a siliceous crystalline molecular sieve at moderate temperature under conditions favorable for conversion of $C_3$-$C_4$ olefins to a second reactor effluent stream rich in heavier hydrocarbons in the gasoline or distillate boiling range.

In addition to lower olefins, the hydrocarbon feed may contain other hydrocarbons such as paraffins (e.g., methane and higher alkanes) as well as inorganic components such as water, $CO_x$ and $N_2$. In such an embodiment of this invention, it has been further found desirable to maintain the pressure in the first reactor zone such that the ethylene partial pressure in the feed contacted with the catalyst in that zone is maintained within the range of about 0.5 to 5 atmospheres.

Oligomerization of olefins according to the method of this invention has been found to allow the catalyst activity to be maintained at a relatively stable level for extended periods of time. Furthermore, the oligomerization process is capable of quantitative conversions of gaseous $C_2+$ olefins to liquid hydrocarbon products with minimal recovery and recycle of process streams to the oligomerization reactors.

BEST MODES FOR CARRYING OUT THE INVENTION

Figure 1:
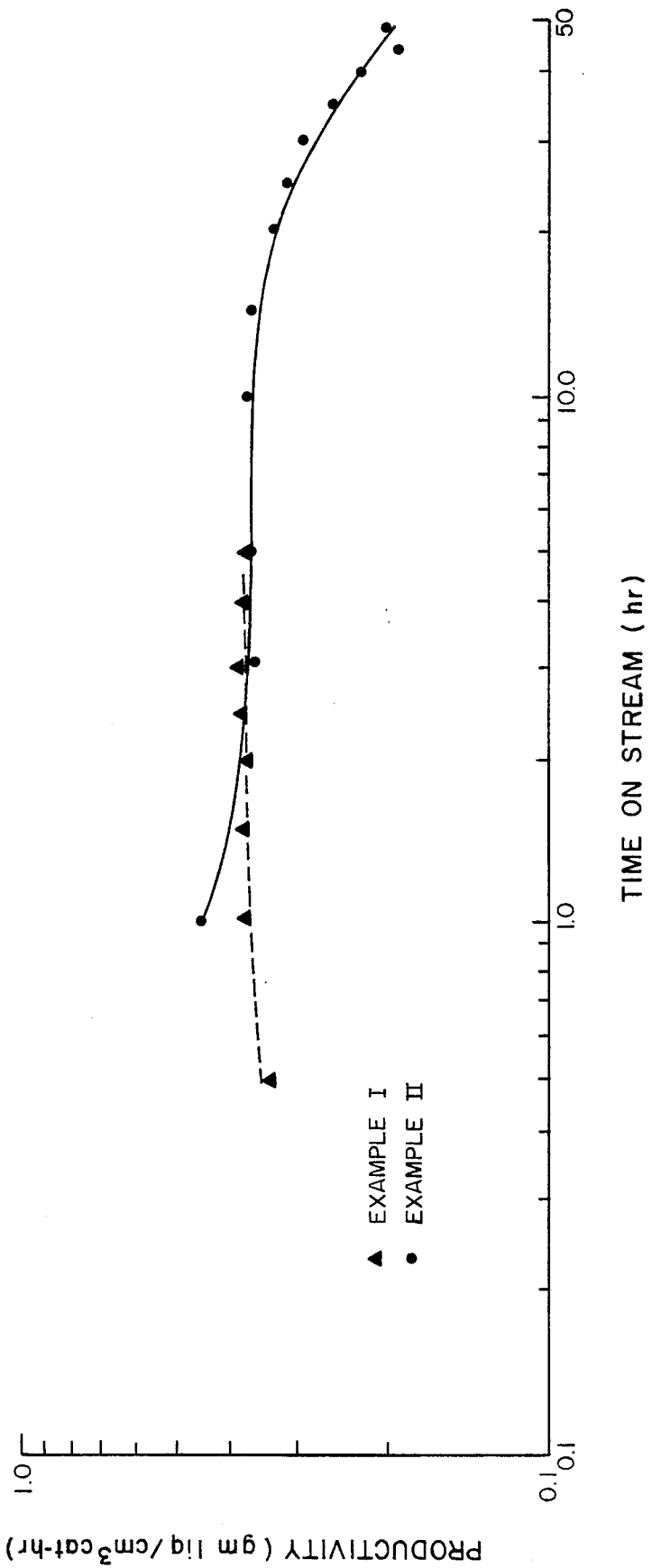
FIG. 1 is a plot of results of run time vs. productivity for catalysts prepared in accordance with Examples I and II.

In the following description of the present invention, the term "WHSV" refers to weight hourly space velocity, esp., weight of ethylene or olefin feed per weight of molecular sieve per hour. WHSV is calculated on the basis of the weight of active catalyst (i.e., molecular sieve) excluding any binders, matrix materials or other inert solid diluents.

The feedstock converted to normal liquid hydrocarbons according to this invention contains ethylene and may also contain $C_3+$ olefins. In addition, the feedstock may contain other hydrocarbon or non-hydrocarbon components. Examples of other hydrocarbon components include the lower alkanes, especially $C_1-C_5$ alkanes. Examples of non-hydrocarbon components include water, carbon oxides (i.e., CO and/or $CO_2$), $N_2$ and the like. The presence of steam in the catalyst reactors zones under the temperature conditions employed is not presently believed to substantially effect the aging and/or the deactivation characteristics of the catalyst. Preferably, the olefins are converted in the substantial absence of hydrogen.

One distinct aspect of the present invention involves the use of highly dilute olefinic feedstocks. More particularly, according to this aspect of the present invention, it has been found that desirable results may be obtained even though the feedstock contains major amounts (i.e., more than 50 vol. %) of lower alkanes. It has further been found that desirable results may be obtained even though the feedstock contains major amounts (i.e., more than 50 vol. %) of methane. When employing such highly dilute olefinic feedstocks in the process of this invention, it has been found advantageous to maintain the ethylene partial pressure in the feed contacted with the catalyst in the first reactor zone within the range of about 0.5 to 5 atmospheres, preferably within the range of about 1 to 2.5 atmospheres. Total operating pressure in the first reactor zone is thus determined by the ethylene content of the feed to the first reactor zone. According to this aspect of the present invention such ethylene content may vary broadly, e.g., within the range of about less than 10 vol. % to 50 vol. %.

As will be apparent to those skilled in the art, the selection of whether to employ such highly dilute, olefinic feedstocks or to first isolate an olefinic fraction of such feedstock prior to oligomerization according to this invention, will be dependent on the cost of processing the highly dilute feedstock via oligomerization relative to the cost of isolating an olefinic fraction therefrom. In general, alkane recovery from oligomerization effluents (particularly the second catalyst rector zone effluent of the process of this invention) is much easier than isolation before oligomerization.

The process of this invention, while not limited thereto in its broader aspects, is particularly suited to oligomerizing feedstocks comprising an olefinic fraction which contains a major amount (i.e., greater than 50 vol. %, preferably greater than 80 vol. %) of ethylene. One observation that led to the present invention was that operating modes favoring direct production of normally liquid hydrocarbons from gaseous olefins (especially from ethylene) also favor the formation of additional gaseous hydrocarbons. For example, the direct conversion of ethylene to normally liquid hydrocarbons also produces substantial amounts of gaseous $C_3+$ hydrocarbons (both olefinic and paraffinic hydrocarbons). Thus, in those sequential processes previously suggested wherein higher olefin oligomerization precedes lower olefin oligomerization, the final effluent will contain significant amounts of lower hydrocarbons which, to optimize yields, must be recovered and recycled through the prior oligomerization steps. One advantage of the present invention is that it minimizes the need for such recovery and recycle.

A related observation is that the formation of additional gaseous hydrocarbon increases as oligomerization severity increases. Thus, direct conversion of propylene to distillate products or aromatic rich products produces more byproduct gaseous hydrocarbons than direct conversion of propylene to olefinic gasoline products, the former conversion requiring higher severity conditions than the latter conversion.

Considering the foregoing observations in the context of the present invention, it has been found desirable to select operating severities for the first catalyst reactor zone that maximize the conversion of ethylene to $C_3-C_4$ olefins and $C_5+$ hydrocarbons. Selection of more severe operating severities—e.g., those that maximize formation of gasoline or distillate products—is not always desirable in the context of this invention. Rather than selecting operating severities to effect conversion of ethylene to a particular product, it is preferable to select operating severities which effect substantially quantitative conversion of ethylene, without rigorous attention to whether, or to what extent, normally liquid hydrocarbons are produced. Having formed a $C_3+$ olefinic, intermediate product in the first reactor zone, the further conversion to normally liquid products may be accomplished with relative ease.

The broad concept of contacting olefins—including mixtures of ethylene with higher hydrocarbons—with a siliceous crystalline molecular sieve to oligomerize the olefins is not novel. A key to one inventive concept of this invention resides in selecting within a limited range of operating conditions such that the following objective will be accomplished in the first catalyst reactor zone: ethylene will be substantially converted to $C_3-C_4$ olefins and $C_5+$ hydrocarbons. Such objective is meant to connote several correlative objectives. For example, ethylene conversion to aromatics in the first catalyst reactor zone will be minimized. Moreover, no attempt is made to maximize conversion of ethylene to normally liquid hydrocarbons in the first reaction zone. While liquids will be formed at operating conditions providing a severity sufficient to maximize ethylene conversion and selectivities to $C_3-C_4$ olefins and $C_5+$ hydrocarbons, hydrocarbon liquid formation is not the principle object to be accomplished in that zone. Furthermore, selecting operating severities for the first reactor zone according, to the method of this invention minimizes the formation of $C_1-C_4$ alkanes. Thus, the gaseous fraction of the first zone effluent is more amenable for further processing to produce normally liquid hydrocarbon products.

The general operating parameters for the first, ethylene oligomerization step of this invention can be defined by stating that the conversion is effected at elevated temperatures and relatively low ethylene partial pressure. By "elevated temperature" is meant a temperature selected within the range of about 285°–425° C., preferably within the range of about 325°–375° C. By "relatively low ethylene partial pressure" is meant a partial pressure within the range of about 0.5 to 5 atmospheres. The space velocity will be one selected within the range of about 0.1 to 20 WHSV, based on ethylene. These ranges of pressure, temperature, and space velocity are not intended to be construed as meaning that all operations with these limits will accomplish the desired results of this invention. Furthermore, as noted previously, use of highly dilute olefinic feedstocks may require relatively high overall pressures to maintain the desired ethylene partial pressure of 0.5 to 5 atmospheres.

What is meant by the foregoing limits is best expressed in a negative way. Operation outside the ranges set forth will not accomplish the desired results of the process of this invention. A well-known correlation exists between temperature, pressure and space velocity with respect to the severity of the reaction. Stated simply, the first step of the present method is concerned with the conversion of ethylene at a severity such that ethylene will be substantially converted to $C_3$–$C_4$ olefins and $C_5+$ hydrocarbons. The examples below illustrate such a severity.

To further illustrate, it is known that if the pressure remains constant and space velocity is increased, then a higher temperature is necessary to achieve the desired severity. Conversely, if the space velocity would remain constant and the pressure increased, then a lower temperature is necessary to achieve the desired severity. The precise space velocity and pressure for any given temperature within the broad range previously stated can be easily obtained by routine experimentation following the guidelines and illustrations set forth herein.

The effluent from the first reactor zone comprises $C_3$–$C_4$ olefins and $C_5+$ hydrocarbons. This effluent is separated by means known to those skilled in the art to produce a normally liquid $C_5+$ hydrocarbon fraction and a $C_3$–$C_4$ olefin fraction. For example, the first stage effluent may be cooled and reduced in pressure by flashing into a phase separation zone to provide a vapor phase rich in $C_3$–$C_4$ olefins and liquid stream rich in $C_5+$ hydrocarbons. The liquid stream may be further processed according to means known in the art. For example, the liquid stream may be upgraded to improve gum stability or may be hydrotreated or may be further converted to form additional distillate products such as diesel and fuel oils. The $C_3$–$C_4$ olefinic fraction which may contain other components, esp. $C_1$–$C_4$ alkanes, is then passed to the second catalytic reactor zone.

Regarding selection of operating conditions to be employed in the second catalyst reactor zone of this invention, the general operating parameters for converting $C_3$–$C_4$ olefins to heavier hydrocarbons in the gasoline and/or distillate boiling range can be defined broadly by stating that the conversion is effected at moderate temperature. By "moderate temperature" is meant a temperature selected within the range of about 150°–330° C. The pressure employed in the second catalyst reactor zone may be vary widely, preferably within the range of about 1 to 70 atmospheres. Similarly, the space velocity may vary widely, generally within the range of about 0.1 to 20 WHSV, based on olefin. Several alternative objectives are within the scope of operation of the second reactor zone of this invention: (1) substantial conversion of $C_3$–$C_4$ olefins to normally liquid hydrocarbons; (2) substantial conversion of $C_3$–$C_4$ olefins to gasoline boiling range hydrocarbons; or (3) substantial conversion of $C_3$–$C_4$ olefins to distillate boiling range hydrocarbons. By "substantial conversion" is meant the conversion of at least 80 wt. %, preferably 90 wt. %, of the $C_3+$ olefins to said products.

Selection of operating parameters suitable to accomplish any of the foregoing objectives have previously been described in the particular context of oligomerization using ZSM-5 type zeolites. See, for example, U.S. Pat. No. 3,760,024 (describes conversion of $C_2$–$C_4$ paraffins and/or olefins); U.S. Pat. No. 3,960,978 (describes conversion of $C_2$–$C_5$ of olefins to a gasoline fraction containing no more than about 20 wt. % aromatics); U.S. Pat. No. 4,021,502 (describes conversion of gaseous olefins to higher molecular weight olefins over ZSM-4, ZSM-12, ZSM-18 chabazite or zeolite beta); and U.S. Pat. No. 4,227,992 (describes selective oligomerization of $C_3+$ olefins to produce fuel oil and gasoline products). The entire content of each of these applications is incorporated by reference.

The comments made above concerning the effect of varying operating temperature, pressure, and space velocity on severity of the first reactor zone apply generally to the effect of such operating conditions on severity in the second reactor zone.

Furthermore, the foregoing descriptions of how to use ZSM-5 type zeolites in the process of this invention also apply to the similar use of other siliceous crystalline molecular sieves. Moreover, the use of borosilicate catalyst and the use of silicalite catalyst in the present process are considered to be distinct aspects of the broader invention generally described herein.

The catalyst employed in the method of this invention are siliceous crystalline molecular sieves. Such silica-containing crystalline materials include materials which contain, in addition to silica, significant amounts of alumina. These crystalline materials are frequently named "zeolites", i.e., crystalline aluminosilicates. However, the use of materials exemplified by silicoaluminoposphates (see U.S. Pat. No. 4,440,871) are also within the scope of this invention. Silica-containing crystalline materials also include essentially aluminum-free silicates. These crystalline materials are exemplified by crystalline silica polymorphs (e.g., silica silicalite, disclosed in U.S. Pat. No. 4,061,724 and organosilicates disclosed in U.S. Pat. No. Re. 29,948), chromiasilicates (e.g., CZM), ferrosilicates and galliosilicates (see U.S. Pat. No. 4,238,318), and borosilicates (see U.S. Pat. Nos. 4,226,420; 4,269,813; and 4,327,236).

The term "essentially aluminum-free" silicates is not intended to totally exclude the presence of aluminum from the catalyst composition. For example, it has been suggested that silicates containing less than 100 ppm. by weight of aluminum may not be effective for the oligomerization of olefins. See U.S. Pat. No. 4,331,641, especially see column 9, lines 49–52 of that patent.

Crystalline aluminosilicate zeolites are best exemplified by ZSM-5 (see U.S. Pat. Nos. 3,702,886 and 3,770,614), ZSM-11 (see U.S. Pat. No. 3,709,979) ZSM-12 (see U.S. Pat. No. 3,832,449), ZSM-21 and ZSM-38 (see U.S. Pat. No. 3,948,758), ZSM-23 (see U.S. Pat. No. 4,076,842), and ZSM-35 (see. U.S. Pat. No. 4,016,246).

The acidic crystalline aluminosilicates are desirably in the hydrogen form, although they may also be stabilized or their performance otherwise enhanced by ion exchange with rare earth or other metal cation.

The molecular sieves can be composited with inorganic matrix materials, or they can be used with an organic binder. It is preferred to use an inorganic matrix since the molecular sieves, because of their large internal pore volumes, tend to be fragile, and to be subject to physical collapse and attrition in normal loading and unloading of the reaction zones as well as during oligomerization processes.

Preferred siliceous crystalline molecular sieves to be employed in the process of this invention are ZSM-5 type zeolites, borosilicates, silicoaluminophosphates and silicalite. ZSM-5 and borosilicate are particularly preferred.

The present invention is further illustrated by reference to the following examples.

EXAMPLE 1

A crystalline borosilicate catalyst was prepared by dissolving $H_3BO_3$ and NaOH in distilled $H_2O$. Then tetra-n-proplyammonium bromide (TPAB) was added and dissolved. Finally, Ludox AS-30(30% solids) was added with vigorous stirring. The addition of Ludox gave a curdy, gelatinous, milky solution. This solution was placed in a vessel and sealed. The vessel was heated to 329° F. (165° C.) for 7 days. At the end of this time, it was opened and its contents were filtered. The recovered crystalline material was washed with copious quantities of $H_2O$ and was then dried at 329° F. (165° C.) in a forced air oven.

The material was calcined at 1,100° F. (593° C.) in air for 4 hours to remove the organic base. The calcined sieve was exchanged one time with an aqueous solution of $NH_4NO_3$ and then a second time with an aqueous ammonium acetate solution at 190° C. (88° C.) for 2 hours. The exchanged borosilicate was dried and calcined in air by heating it to 900° F. (482° C.) in 4 hours, maintaining the borosilicate at 900° C. (482° C.) for 4 hours and then cooling to 100° F. (38° C.) in 4 hours.

The X-ray diffraction pattern is presented in Table I below.

TABLE I

| Interplanar Spacing(A) | Relative Intensity |
|---|---|
| 3.34 | 9 |
| 3.30 | 10 |
| 3.24 | 5 |
| 3.04 | 14 |
| 2.97 | 15 |
| 2.93 | 7 |
| 2.72 | 5 |
| 2.60 | 7 |
| 2.48 | 8 |
| 2.00 | 15 |
| 1.99 | 17 |
| 1.91 | 6 |
| 1.86 | 5 |
| 1.66 | 5 |

EXAMPLE II

An aluminosilicate catalyst was prepared by dissolving 400 grams of N-Brand sodium silicate in ml. of water. Then 150 grams of NaCl, 14.2 grams of $Al_2(SO_4)_3.H_2O$, and 32.9 grams of $H_2SO_4$ was dissolved in 680 ml of $H_2O$. Tetrapropyl ammonium bromide (50 grams) was dissolved in 200 ml of $H_2O$. The sodium silicate solution was mixed with the sodium chloride solution to form a thick, semi-solid mass which was mixed well. The bromide solution was then added to the mixture. The mixture (250 ml.) was charged to an autoclave and was maintained with stirring at 300° F. for 16 hours.

The mixture had a pH of about 12. The solids were washed and decanted until no positive Cl-test was shown with $AgNO_3$. The solids were calcined at 500° C. to produce a white solid.

The material was identified by x-ray diffraction as having the typical ZSM-5 pattern. The x-ray diffraction pattern is presented in Table 2.

TABLE 2

| Interplanar Spacing(A) | Relative Intensity |
|---|---|
| 11.47 | 21 |
| 10.16 | 18 |
| 6.80 | 3 |
| 6.41 | 6 |
| 6.02 | 12 |
| 5.64 | 10 |
| 5.03 | 6 |
| 4.64 | 5 |
| 4.29 | 9 |
| 3.86 | 100 |
| 3.74 | 59 |
| 3.67 | 38 |
| 3.45 | 12 |
| 3.35 | 12 |
| 3.07 | 18 |
| 3.00 | 18 |
| 2.75 | 6 |
| 2.61 | 9 |
| 2.50 | 9 |
| 2.41 | 9 |
| 2.01 | 20 |
| 1.88 | 5 |
| 1.67 | 7 |

EXAMPLE III

The physical characteristics of the materials of Examples I and II were tested and are presented in Table 3 below.

TABLE 3

| | Bulk Density | Al content, wt % | Acidity meq. $NH_3$/gm |
|---|---|---|---|
| Example I | 0.662 | 0.14 | 0.4 |
| Example II | 0.214 | 1.5 | 0.5 |

EXAMPLE IV

Olefin-conversion runs were made at atmospheric pressure and at temperatures between 300°–369° C. in a stainless steel tube reactor packed with 5 ml. of catalyst. The reactors were brought up to temperature under a flow of heated nitrogen which was switched to olefin feed at the start of the run. The olefin-contact runs described had a duration of one hour for Group A, 5 hours for Group B and 50 hours for Group C.

Samples were taken during the run. The gas effluent was collected and measured and analyzed from which a cumulative sample was generated. At the end of each olefin-contact run, the reactor was flushed with nitrogen to cool the reactor and catalyst.

Space velocities are reported as weight hourly space velocities (hr.$^{-1}$) (WHSV). The residence or contact time is also reported. The cumulative results are shown in Tables 4–6 below, the instantaneous results for Run #3 of Table 5 and for the run described in Table 6 are plotted in FIG. 1. Referring to FIG. 1, it can be seen that the oligomerization catalyst is remarkably stable during ethylene conversion according to the first step of the method of this invention.

TABLE 4

| | Group A | |
|---|---|---|
| Feed | Ethylene | |
| Catalyst | Example II | |
| Run Time (hr) | 1 | |
| Temp (°C.) | 350 | |
| Pressure (psig) | 0 | |
| Contact Time (sec) | 0.51 | |
| WHSV (hr$^{-1}$) | 8.1 | |
| $C_2$ = Conv (%) | 99.3 | |

TABLE 4-continued

| Group A | |
|---|---|
| Feed | Ethylene |
| Catalyst | Example II |
| Wt. % Selectivity | |
| $CH_4$ | 1.4 |
| $C_2$ | 1.0 |
| $C_3=$ | 1.7 |
| $C_3$ | 8.1 |
| $C_4=$ | 10.1 |
| $C_4$ | 3.7 |
| $C_5+$ | 75.2 |
| Coke | 0.1 |
| Productivity | 5.9 |
| (# Liquid/# Cat-hr) | |

TABLE 5

| | Group B | | | |
|---|---|---|---|---|
| | Run # | | | |
| | 1 | 2 | 3 | 4 |
| Feed | Propylene | Propylene | Ethylene | Ethylene |
| Catalyst | Example II | Example I | Example I | Example II |
| Run Time (hr) | 5 | 5 | 5 | 5 |
| Temp (°C.) | 300–8 | 300–6 | 350–351 | 350–355 |
| WHSV ($hr^{-1}$) | 4.9 | 1.6 | 0.7 | 2.0 |
| Pressure (psig) | 0 | 0 | 0 | 0 |
| $C_2=$ Conversion (%) | — | — | 99.3 | 99.5 |
| $C_3=$ Conversion (%) | 99.2 | 98.9 | — | — |
| Wt. % Selectivity | | | | |
| $CH_4$ | <0.01 | <0.01 | 0.03 | 0.04 |
| $C_2=$ | 0.2 | 0.1 | — | — |
| $C_2$ | <0.01 | <0.01 | 0.5 | 0.6 |
| $C_3=$ | — | — | 1.2 | 0.7 |
| $C_3$ | 0.8 | 0.2 | 4.9 | 5.9 |
| $C_4=$ | 1.4 | 0.4 | 6.9 | 9.1 |
| $C_4$ | 0.5 | 0.2 | 2.8 | 3.0 |
| $C_5+$ | 96.9 | 98.9 | 80.5 | 80.5 |
| Coke | 0.1 | 0.2 | 0.2 | 0.1 |

TABLE 6

| Group C | |
|---|---|
| Feed | Ethylene |
| Catalyst | Example II |
| Run Time (hr) | 50 |
| Temp (°C.) | 350–369 |
| Press. (psig) | 0 |
| Contact Time (sec) | 2.1 |
| WHSV ($hr^{-1}$) | 2.0 |
| Cumulative $C_2$ = Conv (%) | 88.4 |
| Wt. % Selectivity | |
| $CH_4$ | 0.2 |
| $C_2$ | 0.4 |
| $C_3=$ | 4.3 |
| $C_3$ | 3.1 |
| $C_4=$ | 11.4 |
| $C_4$ | 4.6 |
| $C_5+$ | 76.1 |
| Coke | 0.02 |
| Productivity | 1.3 |
| (# liq/# cat-hr) | 1.3 |
| (gm liq/$cm^3$cat-hr) | 0.3 |

A PONA analysis was conducted on the liquids produced in the run described in Table VI. Results are shown below in Table 7.

TABLE 7

| COMPONENT | WT. % |
|---|---|
| PROPANE | 0.1 |
| PROPYLENE | 0.1 |
| BUTENES | 4.4 |
| i-BUTANE | 2.4 |
| n-BUTANE | 1.3 |
| PENTENES | 10.7 |
| i-PENTANE | 5.6 |
| n-PENTANE | 2.2 |
| TOTAL LIGHT END | 26.8 |

| C# | PARAFFINS | MONOOLEFINS AND MONOCYCLOPARAFFINS | DIOLEFINS AND DICYCLOPARAFFINS | CYCLODIOLEFINS AND TRICYCLOPARAFFINS | ALKYLBENZENES |
|---|---|---|---|---|---|
| 6 | 5.4 | 4.3 | 0.0 | | 0.3 |
| 7 | 4.4 | 7.4 | 0.0 | | 1.5 |
| 8 | 1.7 | 5.1 | 9.6 | | 5.1 |
| 9 | 0.0 | 3.2 | 6.0 | | 5.8 |
| 10 | 0.2 | 1.3 | 2.3 | | 3.1 |
| 11 | 0.0 | 0.6 | 0.9 | | 1.2 |
| 12 | 0.0 | 0.0 | 0.3 | | 0.4 |
| | 11.8 | 22.0 | 19.2 | 1.8 | 17.5 |
| | | | INDANS | 0.8 | |
| | | | NAPHTHALENES | 0.1 | |

EXAMPLE V

Figure 2:
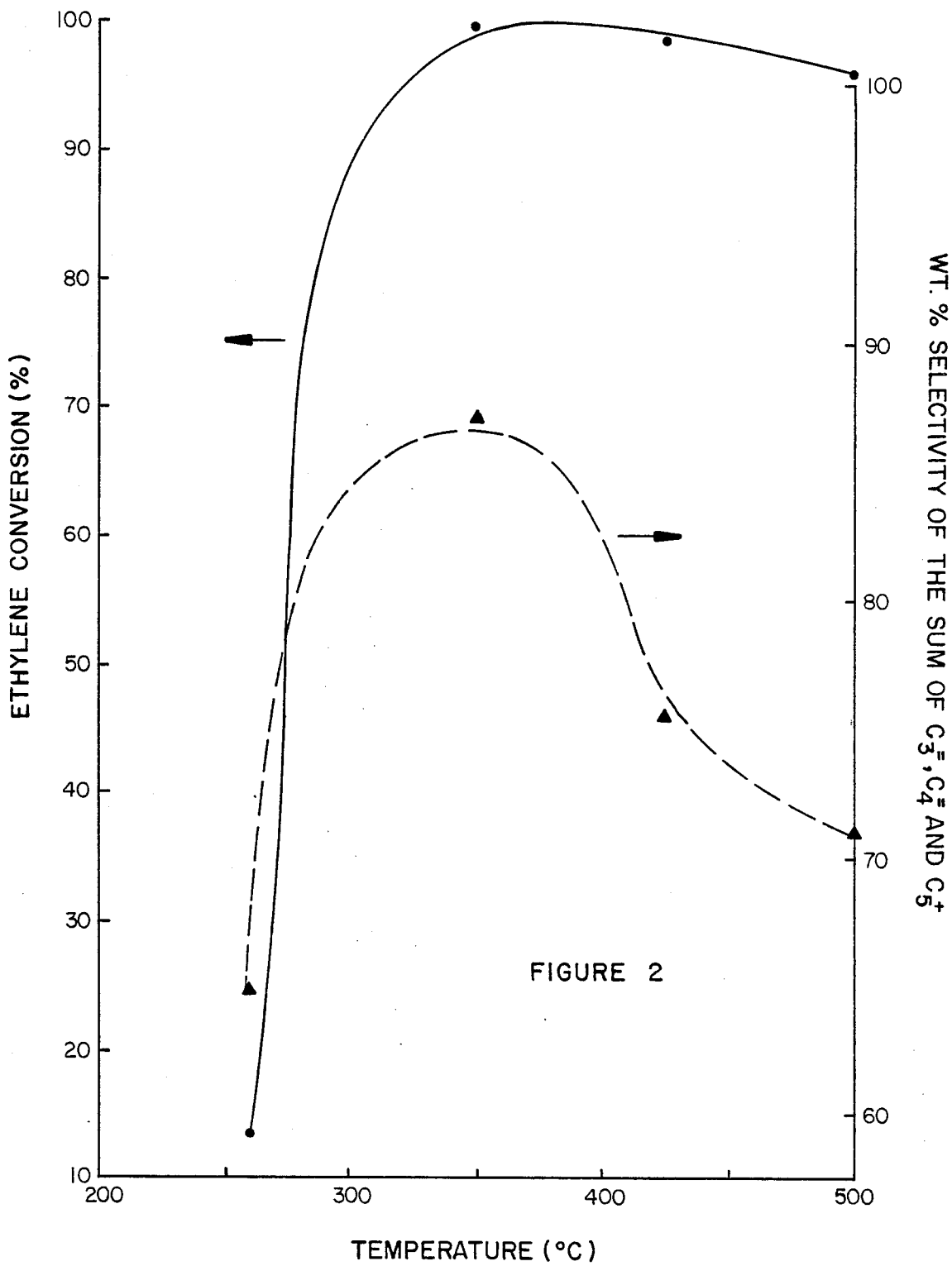
FIG. 2 is a plot of results of temperature vs. ethylene conversion and wt. % selectivity to propylene, butylenes and $C_5+$ hydrocarbons for catalysts prepared in accordance with Example II.

The material prepared in Example I was run under the conditions of Example IV at the temperatures and contact times shown in Table 8. The cumulative run results (obtained during 1 hr. runs) are also shown in Table 8. The total cumulative results obtained as a function of temperature is shown in FIG. 2. Selectivity is reported as the sum of $C_3=$, $C_4=$ and $C_5+$ hydrocarbon in the effluent. Note that as conditions reach the point where significant amounts of ethylene are converted, further increases in severity (i.e., temperature), resulted in a rapid rise of the % ethylene converted to quantitative levels. Further increases in severity had the effect of marginally lowering ethylene conversion. At about the same level of severity where ethylene conversion was quantitative, the wt. % selectivity to $C_3=/C_4=/C_5+$ hydrocarbon products also reached a maximum and the wt. % selectivity to $C_1$-$C_4$ alkanes reached a minimum. As severity was further increased, the wt. % selectivity to $C_3=/C_4=/C_5+$ hydrocarbon products rapidly decreased and the wt. % selectivity to $C_1$-$C_4$ alkanes rapidly increased. Selection of operating conditions to be employed in the ethylene conversion step of the process of the present invention is preferably such that ethylene is substantially quantitatively converted, yielding large quantities of $C_3=$, $C_4=$ and $C_5+$ hydrocarbon products. The yield (i.e., conversion multiplied by selectivity) of these products in the first stage effluent will be greater than about 70 wt. %. The $C_3=$ and $C_4=$ hydrocarbons (i.e., propylene and butylenes) are then converted to normally liquid hydrocarbons in the second stage of this present process. The $C_5+$ hydrocarbons in the first stage effluent are separated prior to the second stage conversion.

TABLE 8

| Temp., °C. | Contact Time, Sec. | % $C_2=$ Conv. | wt. % Selectivity | | | | $C_1$-$C_4$ Alkanes | Productivity (gm. liquid/cm³ catalyst-hr.) |
| --- | --- | --- | --- | --- | --- | --- | --- | --- |
| | | | $C_3=$ | $C_4=$ | $C_5+$ | $C_3=/C_4=/C_5+$ | | |
| 260 | 0.5 | 13.6 | 12.2 | 22.4 | 50.7 | 85.3 | 14.6 | 0.11 |
| 350 | 0.5 | 99.3 | 1.1 | 10.0 | 75.2 | 86.9 | 12.8 | 1.16 |
| 425 | 0.5 | 98.8 | 3.0 | 14.9 | 57.7 | 75.6 | 24.2 | 0.90 |
| 500 | 0.5 | 95.7 | 8.7 | 14.0 | 48.4 | 71.1 | 28.0 | 0.64 |

What is claimed is:

1. A process for converting a feedstock comprising ethylene by catalytic oligomerization to produce heavier hydrocarbons in the gasoline or distillate boiling range which comprises:
   (a) contacting the feedstock in a first catalytic reactor zone with a siliceous crystalline molecular sieve at an elevated temperature within the range of about 285° C. to about 425° C. and a relatively low ethylene partial pressure within the range of about 0.5 to about 5 atmospheres under conditions which maximize: (1) ethylene conversion and (2) selectivities to propylene, butylenes and normally liquid $C_5+$ hydrocarbons;
   (b) separating the effluent stream from step (a) to produce a normally liquid $C_5+$ hydrocarbon fraction and a fraction comprising $C_3$-$C_4$ olefins; and
   (c) contacting the fraction comprising $C_3$-$C_4$ olefins in a second reactor zone with a siliceous crystalline molecular sieve at a moderate temperature within the range of about 150° C. to about 330° C. under conditions favorable for conversion of $C_3$-$C_4$ olefins to a second reactor effluent stream rich in heavier hydrocarbons in the gasoline or distillate boiling range.

2. The process of claim 1 wherein the first and second reactor zones contain an acid ZSM-5 type catalyst.

3. The process of claim 1 wherein the second reactor zone is maintained at a pressure of about 1 to 70 atmospheres.

4. The method of claim 1 wherein the ethylene partial pressure in the feed contacted with catalyst in the first reactor zone is maintained within the range of about 1 to 2.5 atmospheres.

5. The method of claim 1 wherein the feedstock further comprises a hydrocarbon fraction containing a major amount of alkane diluents.

6. The method of claim 5 wherein the alkane diluent comprises a major amount of methane.

7. The method of claim 1 wherein the feedstock further comprises $C_3+$ olefins.

8. The process of claim 1 wherein the first and second reactor zones contain an essentially alumina-free siliceous crystalline molecular sieve.

9. The method of claim 1 wherein the first and second reactor zones contain a borosilicate catalyst.

10. The method of claim 1 wherein the first and second reactor zones contain silicoaluminophosphate catalyst.

11. The method of claim 1 wherein the first and second reactor zones contain silicalite catalyst.

12. The method of claim 7 wherein the feedstock comprises an olefinic fraction containing a major amount of ethylene.

* * * * *